United States Patent [19]

Geiss et al.

[11] Patent Number: 4,772,598

[45] Date of Patent: Sep. 20, 1988

[54] 2-ARYL-3,4-DIAZABICYCLO(4.N.O)ALK-2-EN-5-ONES FOR THE PREPARATION OF AN AGENT FOR TREATING CARDIAC INSUFFICIENCY

[75] Inventors: Karl-Heinz Geiss, Beindersheim, Fed. Rep. of Germany; Phillip A. Rossy, Hilldale, N.J.; Marco Thyes; Horst Koenig, both of Ludwigshafen, Fed. Rep. of Germany; Hans D. Lehmann, Hirschberg, Fed. Rep. of Germany; Martin Traut, Heidelberg, Fed. Rep. of Germany; Josef Gries, Wachenheim, Fed. Rep. of Germany

[73] Assignee: BASF Aktiengesellschaft, Ludwigshafen, Fed. Rep. of Germany

[21] Appl. No.: 914,729

[22] Filed: Oct. 1, 1986

[30] Foreign Application Priority Data

Oct. 2, 1985 [DE] Fed. Rep. of Germany .... 3,535,170

[51] Int. Cl.$^4$ ..................... A61K 31/55; A61K 31/50; A61K 31/495
[52] U.S. Cl. ..................................... 514/213; 514/254
[58] Field of Search ................................ 514/213, 254

[56] References Cited

U.S. PATENT DOCUMENTS 4,474,785 10/1984 Rossy et al. .................... 514/254
4,647,564 3/1987 Robertson ...................... 514/254

FOREIGN PATENT DOCUMENTS 68310 1/1983 European Pat. Off. .
155798 9/1985 European Pat. Off. .

OTHER PUBLICATIONS

Chem. Abst. 98:143,442(e) (1983)–Rossy et al.
Chem. Abst. 107:64872w (1987)–Koenig.
Chem. Abst. 107:70811s (1987)–Geiss et al.

Primary Examiner—Douglas W. Robinson
Attorney, Agent, or Firm—Keil & Weinkauf

[57] ABSTRACT

2-aryl-3,4-diazabicyclo[4.n.0]-alk-2-en-5-ones of the formula

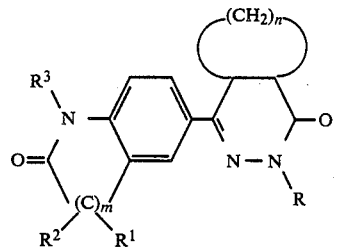

where m, n, R, $R^1$, $R^2$ and $R^3$ have the stated meanings, are used for the treatment of cardiac insufficiency.

5 Claims, No Drawings

2-ARYL-3,4-DIAZABICYCLO(4.N.O)ALK-2-EN-5-ONES FOR THE PREPARATION OF AN AGENT FOR TREATING CARDIAC INSUFFICIENCY

The present invention relates to the use of 2-aryl-3,4-diazabicyclo[4.1.0]hept-2-en-5-ones, 2-aryl-3,4-diazabicyclo[4.2.0]oct-2-en-5-ones and 2-aryl-3,4-diazabicyclo[4.3.0]non-2-en-5-ones in the preparation of an agent for the therapy of cardiac insufficiency.

U.S. Pat. No. 4,474,785 describes diazabicyclo[4.n.-0]alkenones of the general formula I

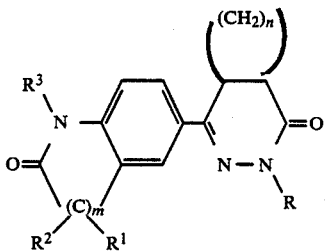

where m and n are identical or different and are each 1, 2 or 3, and R, $R^1$, $R^2$ and $R^3$ are identical or different and are each hydrogen or alkyl of 1 to 6 carbon atoms, and $R^1$ and $R^2$ may be located at the same carbon atom or at different carbon atoms, the said compounds possessing powerful thrombocyte aggregation-inhibiting and hypotensive actions.

EP-A-No. 155 798 describes monocyclic dihydropyridazinones which are similar to those of the present formula I but do not contain a diazabicyclic structure, and have positive inotropic actions.

We have found that the compounds of the formula I have powerful cardiotonic actions, ie. positive inotropic and coronary dilating actions. Furthermore, they inhibit the low $k_m$ cAMP phosphodiesterase. The compounds are accordingly particularly useful cardiotonics for the therapy of the various forms of cardiac insufficiency.

n is preferably 1 or 2, in particular 1, R is preferably hydrogen, and $R^1$, $R^2$ and $R^3$ independently of one another are each preferably hydrogen or methyl and $R^3$ is in particular hydrogen.

Particular examples are:
2-(2,3,4,5-tetrahydrobenzo[b]azepin-2(1H)-on-7-yl)-3,4-diazabicyclo[4.1.0]hept-2-en-5-one and
2-(3,3-trimethylindolin-2-on-5-yl)-3,4-diazabicyclo[4.1.0]hept-2-en-5-one.

The compounds of the formula I are prepared by reacting a cycloalkanecarboxylic acid of the formula II

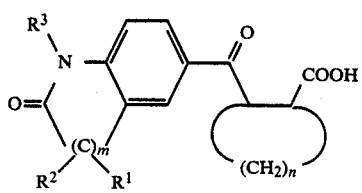

where $R^1$, $R^2$ and $R^3$ have the above meanings, with a hydrazine of the formula $NH_2NHR$, where R has the above meanings.

The cyclization of a compound of the formula II with a hydrazine of the formula $NH_2NHR$, where R has the above meanings, to give a diazabicyclo[4.n.0]alkenone of the formula I is advantageously carried out in a solvent which is inert under the reaction conditions, in particular a lower alcohol, such as methanol, ethanol or propanol, a cyclic aliphatic ether, such as tetrahydrofuran or dioxane, or a dialkylformamide, such as dimethylformamide, and at from 40° to 150° C., preferably from 60° to 120° C. As a rule, from 1 to 1.2 moles of the hydrazine are used per mole of compound of the formula II.

The starting compound of the formula II are obtained by reactin a compound of the formula III

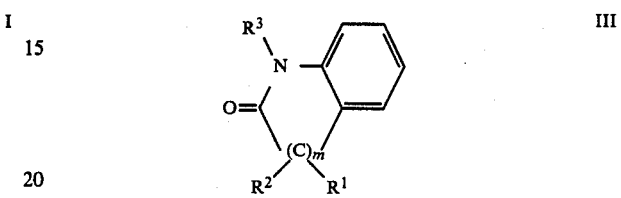

where $R^1$, $R^2$, $R^3$ and m have the above meanings, with 1,2-cyclopropane-, 1,2-cyclobutane- or 1,2-cyclopentanedicarboxylic anhydride in the presence of aluminum chloride under the conditions of a Friedel-Crafts acylation.

This acylation can be carried out in a solvent, for example carbon disulfide, at from 25° to 150° C. It may also be effected in a dimethylformamide/aluminum chloride melt at from 50° to 200° C., preferably from 100° to 160° C. In this process, it is advantageous to use about 10 moles of aluminum chloride and about 2.5 moles of dimethylformamide per mole of 1,2-cyclopropane-, 1,2-cyclobutane- or 1,2-cyclopentanedicarboxylic anhydride and per mole of a compound of the formula II.

It should be pointed out that the compounds of the formula I which are used according to the invention possess asymmetric carbon atoms at positions 1 and 6 of the 3,4-diazabicycloalkenone ring and may possess asymmetric carbon atoms at the 3-position of the indolinone or the 5- or 4-position of the tetrahydroquinolinone ring or the 3-, 4- or 5-position of the tetrahydrobenzo[b]azepinone ring. The invention embraces all enantiomers and diastereomeric forms of compounds of the formula I.

The following methods were used to investigate the pharmacodynamic properties of the novel compounds: The positive inotropic action was demonstrated on 2 to 4 cats weighing from 2.4 to 4.5 kg and anesthetized with 200–330 mg/kg of hexobarbital sodium, administered intramuscularly. It was determined as the increase in the maximum rate of pressure increase $(dp/dt)_{max}$, from the pressure variation in the left ventricle measured by means of tip manometers, and by means of differential amplifiers (Hellige, Freiburg). Administration was effected intravenously in the brachial vein or intraduodenally. 0.5 ml/kg is used for intravenous administration and 1.0 mg/kg for intraduodenal administration.

Method for investigating the inhibition of low $k_m$ cAMP phosphodiesterase:

The enzymatic determination is carried out using the supernatant, obtained under 100,000×g, from the homogenate of human thrombocytes, by the method due to Asano et al [Asano, T., Ochiai, Y. and Midaka, H., Mol. Pharmacol. 13 (1977), 400–406], with $^3$H-labeled cAMP and cGMP as the substrate, in 2 concentrations in each case:

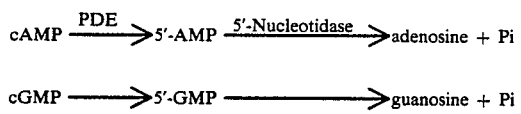

The nucleosides are separated from the starting material over cation exchangers and are quantified in the eluate by $^3$H measurement.

The compounds to be used can be administered in a conventional manner, orally or parenterally (intravenously, intramuscularly or intraperitoneally). The dose depends on the age, condition and weight of the patient and on the route of administration. As a rule, the daily dose of active compound is from about 0.1 to 10 mg/kg of body weight in the case of oral administration and from about 0.01 to 1.0 mg/kg of body weight in the case of parenteral administration. In the normal case, satisfactory results are obtained with daily doses of from 0.5 to 5 mg/kg for oral administration and from 0.05 to 0.5 mg/kg for parenteral administration.

The compounds may be employed in the conventional solid or liquid pharmaceutical forms, such as tablets, film tablets, capsules, powders, granules, coated tablets or suppositories. These are prepared in a conventional manner, and to do so the active compounds can be mixed with the conventional pharmaceutical auxiliaries, such as tablet binders, fillers, preservatives, tablet disintegrators, flow regulators, emulsifiers, solvents, retarding agents, antioxidants and/or propellants (cf. H. Sucker, Pharmazeutische Technologie, Thieme-Verlag, Stuttgart, 1978). The drugs thus obtained normally contain from 1 to 99% by weight of the active compound.

Preparation of the starting compounds (a) 20 ml (0.26 mole) of dimethylformamide are added dropwise to 120 g (0.9 mole) of anhydrous aluminum chloride in the course of a few minutes, while stirring, a highly exothermic reaction taking place. A mixture of 11.8 g (0.089 mole) of indolin-2-one and 11.3 g (0.09 mole) of cyclobutanedicarboxylic anhydride is then added a little at a time at 140° C., after which stirring is continued for a further 10 minutes at this temperature. The melt is then introduced into 0.5 kg of ice. The precipitated solid is filtered off under suction, and the aqueous phase is extracted several times with ethyl acetate. 21.7 g (93.6%) of cis-2-(indolin-2-on-5-oyl)-cyclobutanecarboxylic acid of melting point 211°–212° C. are obtained.

The following are obtained in a similar manner:
(b) cis-2-(1-methylindolin-2-on-5-oyl)-cyclobutanecarboxylic acid, mp. 210°–212° C., yield 84%.
(c) cis-2-(1-indolin-2-on-5-oyl)-cyclopropanecarboxylic acid, mp. 187°–190° C., yield 81%.
(d) cis-2-(1-methylindolin-2-on-5-oyl)-cyclopropanecarboxylic acid, mp. 237°–240° C., yield 81.5%.
(e) cis-2-(1,2,3,4-tetrahydroquinolin-2-on-6-oyl)-cyclobutanecarboxylic acid, mp. 155°–158° C., yield 75%.
(f) cis-2-(1,2,3,4-tetrahydroquinolin-2-on-6-oyl)-cyclopropanecarboxylic acid, mp. 190°–194° C., yield 57%.
(g) cis-2-(2,3,4,5-tetrahydrobenzo[b]azepin-2-(1H)-on-7-oyl)-cyclopropanecarboxylic acid as a pale yellow oil, yield 70%.

Analysis for $C_{15}H_{15}NO_4$ (273): calculated: C 65.9, H 5.5, N 5.1, found: C 65.9, H 5.4, N 4.9.
(h) cis-2-(3,3-dimethylindolin-2-on-5-oyl)-cyclopropanecarboxylic acid, amorphous, yield 58%
(i) cis-2-(3,3-dimethylindolin-2-on-5-oyl)-cyclobutanecarboxylic acid, amorphous, yield 49%.
(k) cis-2-(3,3-dimethyl-1,2,3,4-tetrahydroquinolin-2-on-6-oyl)-cyclopropanecarboxylic acid, amorphous, yield 39%.
(l) cis-2-(3,3-dimethyl-1,2,3,4-tetrahydroquinolin-2-on-6-oyl)-cyclobutanecarboxylic acid, amorphous, yield 55%.
(m) cis-2-(3-methyl-2,3,4,5-tetrahydrobenzo[b]azepin-2-(1H)-on-7-oyl)-cyclopropanecarboxylic acid, amorphous, yield 58%.

EXAMPLE 1

(A) 5.22 g (0.02 mole) of cis-2-(indolin-2-on-5-oyl)-cyclobutanecarboxylic acid are refluxed with 1.1 g (0.022 mole) of hydrazine hydrate and 50 ml of ethanol for 11 hours. The product is filtered off under suction at room temperature and recrystallized from dimethylformamide/water to give 4.7 g (92%) of 2-(indolin-2-on-5-yl)-3,4-diazabicyclo[4.2.0]oct-2-en-5-one of melting point 309°–312° C.

Analysis for $C_{14}H_{13}N_3O_2$ (255): calculated: C 65.8, H 5.1, N 16.5, found: C 65.5, H 5.3, N 16.5.

The following are obtained in a similar manner:
(B) 2-(1-Methylindolin-2-on-5-yl)-3,4-diazabicyclo[4.2.0]oct-2-en-5-one, mp. 256°–259° C., yield 85%.

Analysis for $C_{15}H_{15}N_3O_2$ (269): calculated: C 66.9, H 5.6, N 15.6, found: C 66.6, H 5.7, N 15.5.

(C) 2-(Indolin-2-on-5-yl)-3,4-diazabicyclo[4.1.0]hept-2-en-5-one, mp. 305°–307° C., yield 81%

Analysis for $C_{13}H_{11}N_3O_2$ (241): calculated: C 64.7, H 4.6, N 17.4, found: C 64.7, H 4.6, N 17.5.

(D) 2-(1-Methylindolin-2-on-5-yl)-3,4-diazabicyclo[4.1.0]hept-2-en-5-one, mp. 265°–267° C., yield 51%

Analysis for $C_{14}H_{13}N_3O_2$ (255): calculated: C 65.9, H 5.1, N 16.5, found: C 65.4, H 5.1, N 17.0.

(E) 2-(1,2,3,4-Tetrahydroquinolin-2-on-6-yl)-3,4-diazabicyclo[4.2.0]oct-2-en-5-one, mp. 349°–353° C., yield 84%.

Analysis for $C_{15}H_{15}N_3O_2$ (269): calculated: C 66.9, H 5.6, N 15.6, found: C 66.7, H 5.6, N 15.5.

(F) 2-(1,2,3,4-Tetrahydroquinolin-2-on-6-yl)-3,4-diazabicyclo[4.1.0]hept-2-en-5-one, mp. 310°–311° C. (decomposition), yield 75%.

Analysis for $C_{14}H_{13}N_3O_2 \times \frac{1}{2}H_2O$: calculated: C 64.8, H 5.2, N 16.4, found: C 64.7, H 5.2, N 16.2.

(G) 2-(1,2,3,4-Tetrahydroquinolin-2-on-6-yl)-4-methyl-3,4-diazabicyclo[4.1.0]hept-2-en-5-one, mp. 255°–259° C., yield 76%

Analysis for $C_{15}H_{15}N_3O_2$ (269): calculated: C 66.9, H 5.6, N 15.6, found: C 66.6, H 5.7, N 15.5.

(H) 2-(2,3,4,5-Tetrahydrobenzo[b]azepin-2-(1H)-on-7-yl)-3,4-diazabicyclo[4.1.0]hept-2-en-5-one, mp. 308°–310° C. (decomposition), yield 75%.

Analysis for $C_{15}H_{15}N_3O_2$ (269): calculated: C 66.9, H 5.6, N 15.6, found: C 66.2, H 5.3, N 15.4.

(I) 2-(3,3-Dimethylindolin-2-on-5-yl)-3,4-diazabicyclo[4.1.0]hept-2-en-5-one, mp. 334°–335° C., yield 71%.

Analysis for $C_{15}H_{15}N_3O_2$ (269): calculated: C 66.9, H 5.6, N 15.6, found: C 66.7, H 5.7, N 15.5.

(K) 2-(3,3-Dimethylindolin-2-on-5-yl)-3,4-diazabicyclo[4.2.0]oct-2-en-5-one, mp. 315°–317° C., yield 55%

Analysis for $C_{16}H_{15}N_3O_2 \cdot 0.1H_2O$: calculated: C 67.39, H 6.08, N 14.74, found: C 67.0, H 6.1, N 14.7.

(L) 2-(3,3-Dimethyl-1,2,3,4-tetrahydroquinolin-2-on-6-yl)-3,4-diazabicyclo[4.1.0]hept-2-en-5-one, mp. 275°–277° C., yield 62%

Analysis for $C_{16}HH_{17}N_3O_2.0.1H_2O$: calculated: C 67.39, H 6.08, N 14.74, found: C 67.0, H 6.2, N 14.9.

(M) 2-(3,3-Dimethyl-1,2,3,4-tetrahydroquinolin-2-on-6-yl)-3,4-diazabicyclo[4.2.0]oct-2-en-5-one, mp. 301°–302° C., yield 81%

(N) 2-(3-Methyl-2,3,4,5-tetrahydrobenzo[b]azepin-2-(1H)-on-7-yl)-3,4-diazabicyclo[4.1.0]hept-2-en-5-one, mp. 305°–307° C., yield 21%

Analysis for $C_{15}H_{15}N_3O_2$ (269): calculated: C 64.8, H 5.2, N 16.4, found: C 64.7, H 5.2, N 16.2.

(O) 2-(3-Methylindolin-2-on-5-yl)-3,4-diazabicyclo[4.1.0]hept-2-en-5-one (P) 2-(3,3-Diethylindolin-2-on-5-yl)-3,4-diazabicyclo[4.1.0]hept-2-en-5-one (Q) 2-(1,3,3-Trimethylindolin-2-on-5-yl)-3,4-diazabicyclo[4.1.0]hept-2-en-2-onen-5-one (R) 2-(3-Methyl-1,2,3,4-tetrahydroquinolin-2-on-6-yl)-3,4-diazabicyclo[4.1.0]hept-2-en-5-one (S) 2-(3-Ethyl-1,2,3,4-tetrahydroquinolin-2-on-6-yl)-3,4-diazabicyclo[4.1.0]hept-2-en-5-one (T) 2-(4-Methyl-1,2,3,4-tetrahydroquinolin-2-on-6-yl)-3,4-diazabicyclo[4.1.0]non-2-en-5-one (U) 2-(3,3-Diethyl-1,2,3,4-tetrahydroquinolin-2-on-6-yl)-3,4-diazabicyclo[4.1.0]hept-2-en-5-one (V) 2-(1,3-Dimethyl-1,2,3,4-tetrahydroquinolin-2-on-6-yl)-3,4-diazabicyclo[4.1.0]hept-2-en-5-one (W) 2-(1,4-Dimethyl-1,2,3,4-tetrahydroquinolin-2-on-6-yl)-3,4-diazabicyclo[4.1.0]hept-2-en-5-one (X) 2-(1,3,3-Trimethyl-1,2,3,4-tetrahydroquinolin-2-on-6-yl)-3,4-diazabicyclo[4.1.0]hept-2-en-5-one

FORMULATION EXAMPLES

I. Tablets having the following composition are prepared:

| Active compound | 10 mg |
|---|---|
| Polyvinylpyrrolidone (mean molecular weight 25,000) | 170 mg |
| Polyethylene glycol (mean molecular weight 4,000) | 14 mg |
| Hydroxypropylmethylcellulose | 40 mg |
| Talc | 4 mg |
| Magnesium stearate | 2 mg |
| | 240 mg |

The active compound is moistened with a 10% strength aqueous solution of polyvinylpyrrolidone and forced through a sieve of 1.0 mm mesh size, and the granules are dried at 50° C. They are then mixed with polyethylene glycol (mean molecular weight 4,000), hydroxypropylmethylcellulose, talc and magnesium stearate, and the mixture is pressed to give tablets weighing 240 mg.

II. Coated tablets having the following composition are prepared:

| Active compound | 10 mg |
|---|---|

-continued

| Lactose | 90 mg |
|---|---|
| Corn starch | 60 mg |
| Polyvinylpyrrolidone | 6 mg |
| Magnesium stearate | 1 mg |
| | 167 mg |

The active compound, lactose and corn starch are mixed, moistened with an 8% strength aqueous solution of polyvinylpyrrolidone and granulated by being passed through a 1.5 mm sieve. The granules are dried at 50° C. and forced through a 1.0 mm sieve. The granules thus obtained are mixed with magnesium stearate, and the mixture is pressed to form tablet cores. These are coated in a conventional manner with a shell consisting essentially of sugar and talc.

We claim:

1. The method of treating cardiac insufficiency in a patient suffering therefrom which comprises administering enterally or parenterally to said patient a cardiotonic effective amount of a 2-aryl-3,4-diazabicyclo[4.1.0]alk-2-en-5-one of the formula I

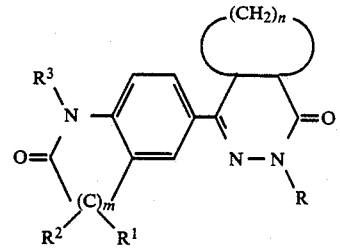

where m and n are identical or different and are each 1, 2 or 3 and R, $R^1$, $R^2$ and $R^3$ are identical or different and are each hydrogen or alkyl of 1 to 6 carbon atoms.

2. The method of treating cardiac insufficiency in a patient suffering therefrom which comprises administering enterally or parenterally to said patient a cardiotonic effective amount of a compound of the formula I where m is 1, 2 or 3, n is 1 or 2, R is H, and $R^1$, $R^2$ and $R^3$ independently from each other are hydrogen or methyl.

3. The method of treating cardiac insufficiency in a patient suffering therefrom which comprises administering enterally or parenterally to said patient a cardiotonic effective amount of a compound of the formula I where m is 1, 2 or 3, n is 1, R and $R^3$ are each H, $R^1$ and $R^2$ are independently of each other are hydrogen or methyl.

4. The method of treating cardiac insufficiency in a patient suffering therefrom which comprises administering enterally or parenterally to said patient a cardiotonic effect amount of a compound of the formula I where m is 3, n is 1, and R, $R^1$, $R^2$ and $R^3$ are H.

5. The method of treating cardiac insufficiency in a patient suffering therefrom which comprises administering enterally or parenterally to said patient a cardiotonic effective amount of a compound of the formula I where m and n are each 1, R and $R^3$ are each H and $R^1$ and $R^2$ are each methyl.

* * * * *